United States Patent
Fu (10) Patent No.: US 10,782,423 B2
(45) Date of Patent: Sep. 22, 2020

(54) MECHANICAL LINKAGE SYSTEM OF PET AND CT/MRI AND LINKAGE SCANNING METHOD THEREOF

(71) Applicant: BEIJING NEUSOFT MEDICAL EQUIPMENT CO., LTD., Beijing (CN)

(72) Inventor: Changqing Fu, Shenyang (CN)

(73) Assignee: Beijing Neusoft Medical Equipment Co., Ltd., Beijing (CN)

( * ) Notice: Subject to any disclaimer, the term of this patent is extended or adjusted under 35 U.S.C. 154(b) by 0 days.

(21) Appl. No.: 15/712,501

(22) Filed: Sep. 22, 2017

(65) Prior Publication Data

US 2018/0088245 A1 Mar. 29, 2018

(30) Foreign Application Priority Data

Sep. 23, 2016 (CN) .......................... 2016 1 0847248

(51) Int. Cl.
*G01T 1/163* (2006.01)
*A61B 6/03* (2006.01)
(Continued)

(52) U.S. Cl.
CPC .......... *G01T 1/1635* (2013.01); *A61B 5/0035* (2013.01); *A61B 5/055* (2013.01);
(Continued)

(58) Field of Classification Search
CPC ... G01T 1/1635; G01T 1/1603; G01T 1/1611; G01T 1/2985; A61B 5/0035;
(Continued)

(56) References Cited

U.S. PATENT DOCUMENTS 3,651,256 A * 3/1972 Sherman .................. H04N 3/08
358/489
5,125,791 A * 6/1992 Volovich ............... H01L 21/681
198/394
(Continued)

FOREIGN PATENT DOCUMENTS

CN 202684531 U 1/2013
CN 103608698 A 2/2014
(Continued)

OTHER PUBLICATIONS

European Patent Office: European Search Report mailed in corresponding European Patent Application No. 17192929.2 dated Feb. 22, 2018 (8 pages).
(Continued)

*Primary Examiner* — Blake C Riddick
(74) *Attorney, Agent, or Firm* — Fish & Richardson P.C.

(57) ABSTRACT

A mechanical linkage system of PET and CT/MRI and a linkage scanning method thereof are disclosed. According to an example of the disclosure, the mechanical linkage system includes a PET host, a CT/MRI host, a scanning bed, and a moving system. The PET host includes a PET detector installed in a PET detector fixing plate and configured to form a positron emission computed tomography image. The CT/MRI host has a larger aperture than the PET detector. A front end of the PET host and a front end of the CT/MRI host are oppositely disposed. The scanning bed is located to an end of the CT/MRI host. The moving system is connected with at least one of the PET host or the CT/MRI host and configured to move the PET detector into or out of a scanning field of view of the CT/MRI host.

18 Claims, 9 Drawing Sheets

(51) Int. Cl.
*A61B 6/00* (2006.01)
*G01R 33/48* (2006.01)
*A61B 5/00* (2006.01)
*A61B 5/055* (2006.01)
*A61B 6/04* (2006.01)
*G01T 1/16* (2006.01)
*G01T 1/161* (2006.01)
*G01T 1/29* (2006.01)

(52) U.S. Cl.
CPC ............... *A61B 6/03* (2013.01); *A61B 6/032* (2013.01); *A61B 6/037* (2013.01); *A61B 6/04* (2013.01); *A61B 6/4417* (2013.01); *G01R 33/481* (2013.01); *G01T 1/1603* (2013.01); *G01T 1/1611* (2013.01); *G01T 1/2985* (2013.01); *A61B 5/0037* (2013.01); *A61B 6/5247* (2013.01)

(58) Field of Classification Search
CPC ......... A61B 5/0037; A61B 5/055; A61B 6/03; A61B 6/032; A61B 6/037; A61B 6/04; A61B 6/4417; A61B 6/5247; G01R 33/481
USPC ............ 250/363.02, 363.03, 363.04, 363.05, 250/363.08
See application file for complete search history.

(56) References Cited

U.S. PATENT DOCUMENTS

| | | | | |
|---|---|---|---|---|
| 5,391,866 A * | 2/1995 | Hoshino | ............... | G02B 7/10 250/201.2 |
| 5,550,886 A * | 8/1996 | Dobbs | ............... | A61B 6/032 378/19 |
| 7,531,773 B2 * | 5/2009 | Westerweck | ......... | G01D 5/3473 250/201.5 |
| 2006/0108536 A1 * | 5/2006 | Hwang | ............... | G01K 1/08 250/397 |
| 2007/0238950 A1 * | 10/2007 | Vija | ............... | A61B 6/032 600/407 |
| 2008/0001089 A1 | 1/2008 | Lusser | | |
| 2008/0039712 A1 * | 2/2008 | Graves | ............... | A61B 5/055 600/411 |
| 2009/0102457 A1 * | 4/2009 | Vayner | ............... | G01R 31/2889 324/756.01 |
| 2010/0041991 A1 * | 2/2010 | Roundhill | ............... | A61B 8/4281 600/443 |
| 2010/0135454 A1 * | 6/2010 | Noo | ............... | G06T 11/006 378/9 |
| 2011/0261926 A1 * | 10/2011 | Hangartner | ............... | A61B 6/032 378/19 |
| 2013/0241555 A1 | 9/2013 | Obata et al. | | |
| 2014/0124658 A1 * | 5/2014 | Xie | ............... | E05F 15/622 250/236 |
| 2015/0045653 A1 | 2/2015 | Okamoto et al. | | |
| 2016/0038029 A1 * | 2/2016 | Darne | ............... | A61B 5/0071 600/427 |
| 2016/0183890 A1 | 6/2016 | Nathan | | |

FOREIGN PATENT DOCUMENTS

| | | | |
|---|---|---|---|
| CN | 104044749 A | * | 9/2014 |
| CN | 104044749 A | | 9/2014 |
| CN | 104458776 A | | 3/2015 |
| CN | 205251561 U | | 5/2016 |

OTHER PUBLICATIONS

State Intellectual Property Office of the People's Republic of China, Office Action and Search Report mailed in counterpart Chinese patent application No. 201610847248.0, dated Feb. 2, 2019, 20 pages (with English-language machine translation).

* cited by examiner

MECHANICAL LINKAGE SYSTEM OF PET AND CT/MRI AND LINKAGE SCANNING METHOD THEREOF

CROSS REFERENCE TO RELATED APPLICATIONS

This application claims priority under 35 U.S.C. § 119 to Chinese Patent Application No. 201610847248.0 filed on Sep. 23, 2016, the entire content of which is incorporated herein by reference for all purposes.

TECHNICAL FIELD

The present disclosure relates to the field of medical device technologies, particularly to a mechanical linkage system of Positron Emission Tomography (PET) and Computed Tomography/Magnetic Resonance Imaging (CT/MRI) and a linkage scanning method thereof.

BACKGROUND

Devices, such as a PET device, a CT device, and an MRI device, are typical medical imaging devices. Two or more of the devices may form, by combination, a device that may continuously complete a plurality of scanning imaging tasks, e.g., where a CT/MRI device may be used for attenuation correction of a PET, which has the advantages of short scanning time, low noise and so on, so as to replace a transmission scan and shorten the time of whole body imaging. CT/MRI images may also be used for lesion positioning.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128. Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods and systems for mechanically linkage of PET and CT/MRI and associated linkage scanning, which can address the problem that a device is inconvenient to install and transport and has high manufacturing cost due to a large volume and also the problem that an image diagnosis is influenced as a fusion image is inaccurate due to a far travelling distance of a scanning bed and/or movement of a patient. Implementations of the present disclosure realize scanning with a common field of view by moving a PET device and/or a CT/MRI imaging device, which may greatly reduce the travelling distance of a scanning bed, thereby reducing the amount of deformation of the bed board of the scanning bed and improving the accuracy of a fusion image.

One aspect of the present disclosure features a mechanical linkage system of Positron Emission Tomography (PET) and Computed Tomography/Magnetic Resonance Imaging (CT/MRI). The system includes: a PET host having a PET detector; a CT/MRI host including a CT host or an MRI host disposed opposite to the PET host, the CT/MRI host having an aperture larger than an aperture of the PET detector; a scanning bed located to an end of the CT/MRI host; and a moving system connected with at least one of the PET host or the CT/MRI host such that the PET detector is operable to be moved into or out of a scanning field of view of the CT/MRI host.

The CT host can include: a CT rotation system having an aperture larger than the aperture of the PET detector; a CT tube installed on an end of the CT rotation system and adjacent to the PET detector; and a CT detector installed on the end of the CT rotation system and adjacent to the PET detector, the CT detector being disposed opposite to the CT tube. The MRI host can include an MRI magnet having an aperture larger than the aperture of the PET detector.

In some implementations, the PET host includes a PET detector fixing plate on which the PET detector is installed, and the moving system includes a transmission device connected with the PET detector fixing plate.

In some examples, the transmission device includes: a driving motor; two or more rotating screws respectively connected with one of an inner side and an outer side of the PET detector fixing plate; respective rotating wheels installed on the rotating screws, where a rotating wheel on one of the rotating screws is a main rotating wheel, and the driving motor is in transmission connection with the main rotating wheel; and a driving belt connecting the rotating screws. The rotating screws can be evenly distributed along a same circumference of the PET detector fixing plate.

In some cases, the rotating screws can be connected with the outer side of the PET detector fixing plate, and the moving system can include a screw connecting chamber, and an inner edge of the screw connecting chamber is connected with a respective outer edge of each of the rotating screws. In some cases, the driving motor and the main rotating wheel are connected by one of a second driving belt of the main rotating wheel and a gear.

In some implementations, the PET host includes a PET detector connecting chamber, the PET detector can be connected inside the PET detector connecting chamber, and the moving system can include a movable base connected with at least one of the PET host or the CT/MRI host.

In some examples, the moving system includes a movable base installed at a bottom of the PET host. In some examples, the moving system includes a movable base installed at bottoms of the CT/MRI host and the scanning bed. In some examples, the moving system includes two movable bases installed at a bottom of the PET host and a bottom of the CT/MRI host, respectively.

Another aspect of the present disclosure features a linkage scanning method. The method includes: performing a pilot image scanning with a CT/MRI host; performing a CT helical scanning or an MRI axial scanning with the CT/MRI host; moving a PET detector of the PET host to be in a scanning field of view of the CT/MRI host by a displacement of a moving system; collecting PET data with the PET detector; and after the PET data collection is completed, moving the PET detector to be out of the scanning field of view of the CT/MRI host by the moving system.

In some implementations, the moving system includes a transmission device connected with a PET detector fixing plate on which the PET detector is installed. Moving the PET detector to be in the scanning field of view of the CT/MRI host by the displacement of the moving system includes: driving a first driving belt of a main rotating wheel to rotate by a rotation of a driving motor, driving the main rotating wheel to rotate by the first driving belt of the main rotating wheel, driving a second driving belt by the rotation of the main rotating wheel, and driving rotating wheels of other rotating screws to rotate by the second driving belt, so as to drive the PET detector fixing plate to move, such that the PET detector is moved forward or backward to ultimately be in the scanning field of view of the CT/MRI host.

In some implementations, the moving system is a transmission device connected with a PET detector fixing plate on which the PET detector is installed, and moving the PET detector to be in the scanning field of view of the CT/MRI host by the displacement of the moving system includes: driving a main rotating wheel of a rotating screw to rotate by a rotation of a driving motor through a gear, driving a driving belt by the rotation of the main rotating wheel, and driving rotating wheels of other rotating screws to rotate by the driving belt, so as to drive the PET detector fixing plate to move, such that the PET detector is moved forward or backward to ultimately be in the scanning field of view of the CT/MRI host.

In some implementations, the moving system includes a movable base installed at a bottom of a PET host, and moving the PET detector to be in the scanning field of view of the CT/MRI host by the displacement of the moving system includes: moving the PET host forward or backward by moving the movable base such that the PET detector is ultimately in the scanning field of view of the CT host or the MRI host.

In some implementations, the moving system includes a movable base installed at bottoms of the CT/MRI host and the scanning bed, and moving the PET detector to be in the scanning field of view of the CT/MRI host by the displacement of the moving system includes: moving the CT/MRI host and the scanning bed forward or backward by moving the movable base such that the PET detector is ultimately in the scanning field of view of the CT host or the MRI host.

In some implementations, the moving system comprises two movable bases installed at bottoms of the PET host and the CT/MRI host, respectively, and moving the PET detector to be in the scanning field of view of the CT/MRI host by the displacement of the moving system includes: moving the PET host and the CT/MRI host towards each other by moving the two movable bases such that the PET detector is in the scanning field of view of the CT/MRI host.

A further aspect of the present disclosure features a linkage system including: a first modal host having a first modal detector and a first receiving chamber; a second modal host disposed oppositely to the first modal host and having a second receiving chamber with an aperture larger than an aperture of the first receiving chamber; and a moving system connected with at least one of the first modal host or the second modal host and configured to move the at least one of the first modal host or the second modal host such that the first modal detector is operable to be moved into or out of the second receiving chamber of the second modal host.

The linkage system can further include a scanning bed placed to an end of the second modal host. The first modal host is located to the other end of the second modal host opposite to the scanning bed.

In one embodiment, the first modal host is a PET host and the second modal host is a CT host or an MRI host. The first receiving chamber of the first modal host is a receiving chamber formed by a PET detector and capable of receiving a scanning bed, and the aperture of the first receiving chamber is an aperture of the PET detector. The second receiving chamber of the second modal host is a receiving chamber formed by the CT detector and capable of receiving the scanning bed. In another embodiment, the first modal host may be a CT host or an MRI host, and the second modal host may be a PET host. The first receiving chamber of the first modal host is a receiving chamber formed by the CT host. The second receiving chamber of the second modal host is a receiving chamber formed by a PET detector. In yet another embodiment, the first modal host may be a host of another type of device, and the second modal host may also be a host of another type of device, but it is not limited thereto. In some embodiments, the scanning bed is placed to an end of the second modal host and the first modal host is located to the other end of the second modal host opposite to the scanning bed.

The details of one or more embodiments of the subject matter described in the present disclosure are set forth in the accompanying drawings and description below. Other features, aspects, and advantages of the subject matter will become apparent from the description, the drawings, and the claims.

DETAILED DESCRIPTION

A PET-CT/MRI system includes a PET host and a CT/MRI host that can be relatively independent and have respective own gantries. For example, the gantry of the CT/MRI host is in the front and the gantry of the PET host is in the back, or the gantry of the PET host is in the front and the gantry of the CT/MRI host is in the back. The system has a large size, which may result in inconvenient in installation and transportation and high manufacturing cost. In addition, when scanning patients, if the two independent host gantries have a far relative distance, a bed board of a scanning bed may have travelled a far distance before a scanning field of view of a front host appears in a scanning field of view of a back host. The bed board may produce a particular deformation, which may cause an inaccurate fusion image and influence an image diagnosis.

In some cases, a PET-CT/MRI system includes a CT/MRT host and a PET host in two different places. A patient has to go to the two different places for scanning. Thus, after CT/MRI scanning is completed in a first place, it is necessary to move the patient to a second, different place for PET scanning, which not only increases scanning time but also increases error when CT/MRI and PET images are fused, thereby causing the fusion image to be inaccurate and influencing the image diagnosis.

Implementations of the present disclosure provide a mechanical linkage system of PET and CT/MRI. The system can include a PET host, a CT/MRI host (i.e., a CT host or an MRI host), a scanning bed and a moving system, where the PET host includes a PET detector and a PET detector fixing plate. The PET detector is installed in the PET detector fixing plate and configured to form a positron emission computed tomography image. The CT/MRI host includes a CT host or an MRI host, and the CT/MRI host has a larger aperture than the PET detector. A front end of the PET host and a front end of the CT/MRI host are oppositely disposed. The scanning bed is disposed at a rear end of the CT/MRI host, and the scanning bed is provided with a bed board which may be moved back and forth to allow a patient to lie flat. The moving system is connected with the PET host and/or the CT/MRI host and configured to move the PET detector into or out of the scanning field of view of the CT/MRI host.

Figure 1:
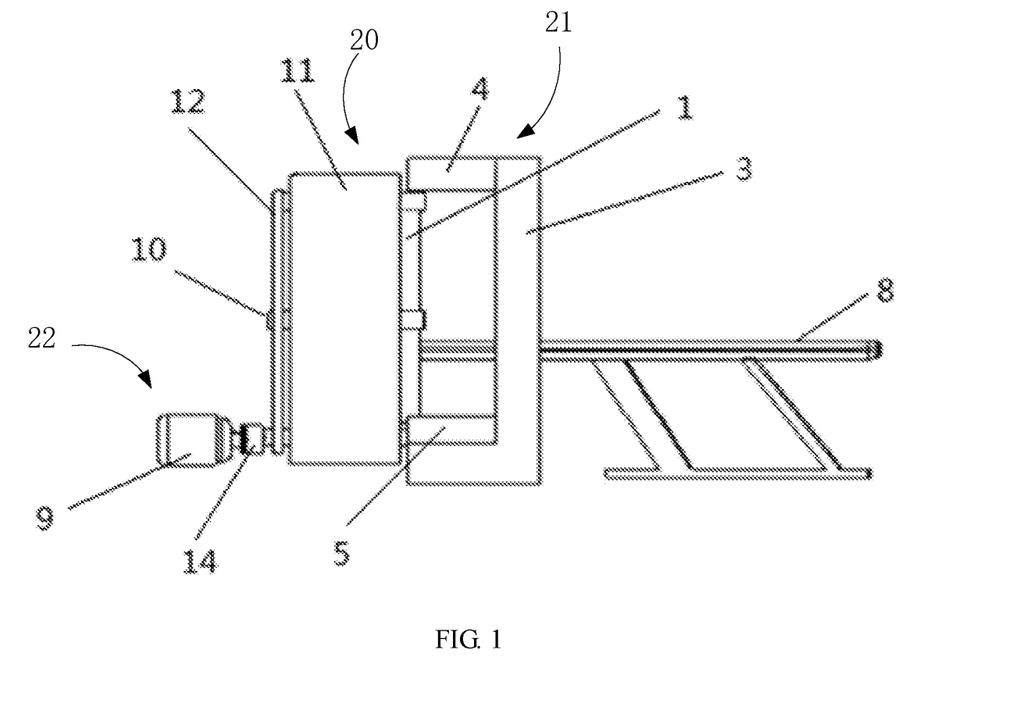
FIG. 1 is a structure schematic diagram of a mechanical linkage system of PET and CT in accordance with one example of the present disclosure.
Figure 2:
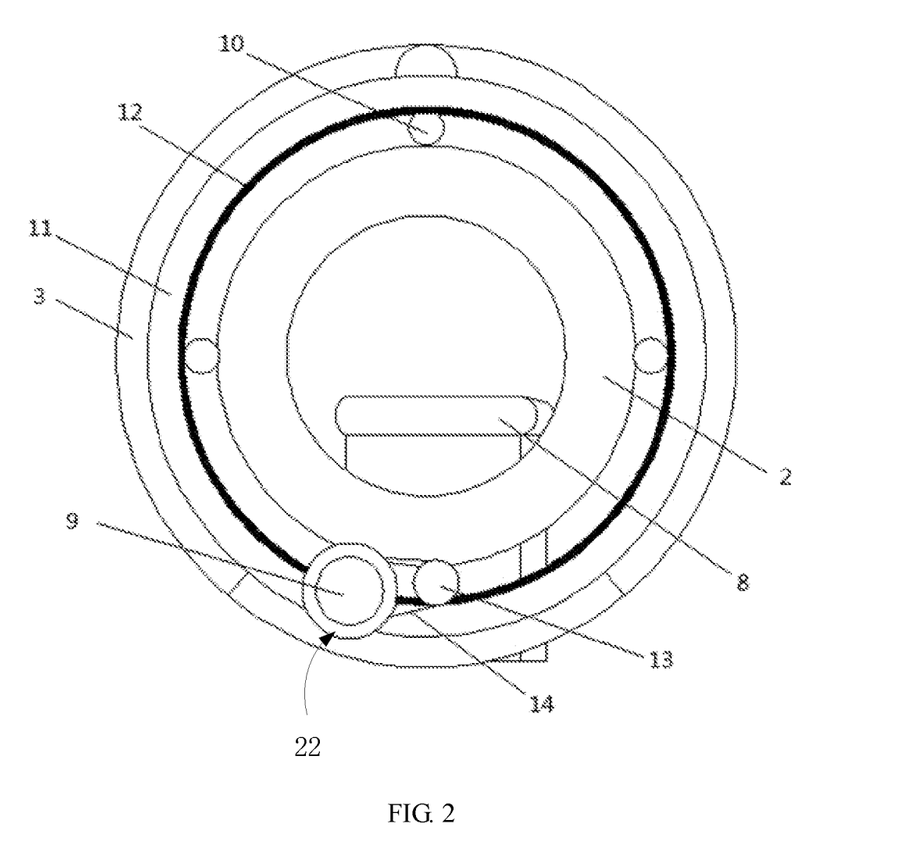
FIG. 2 is a structure schematic diagram of a left side of the mechanical linkage system of PET and CT shown in FIG. 1.

FIG. 1 shows a schematic diagram of a mechanical linkage system of PET and CT/MRI in accordance with one example of the present disclosure. As shown in FIG. 1, in the illustrated embodiment, the mechanical linkage system of PET and CT/MRI is a mechanical linkage system of PET and CT, and may include a PET host 20, a CT host 21, and a scanning bed 8. The PET host 20 includes a PET detector 1 and a PET detector fixing plate 2 (as shown in FIG. 2), and the PET detector 1 is installed on the PET detector fixing plate 2. The CT host 21 includes a CT rotation system 3, a CT tube 4 and a CT detector 5. The CT tube 4 and the CT detector 5 are installed on one side of the CT rotation system 3 which is close to the PET detector 1. The CT tube 4 and the CT detector 5 are disposed oppositely. An aperture of the CT rotation system 3 is larger than an aperture of the PET detector 1. For example, the aperture of the CT rotation system 3 is larger than an external diameter of the PET detector 1. The mechanical linkage system also includes a moving system. In some embodiments, the moving system includes a transmission device 22 installed at a rear end of the PET host 20 for moving the PET detector 1 into or out of a scanning field of view of the CT detector 5.

Specifically, as shown in FIG. 2, the transmission device 22 includes a driving motor 9, two or more rotating screws 10, a driving belt 12, and a screw connecting chamber 11. Each of the rotating screws 10 is connected to the outer side of the PET detector fixing plate 2. The inner edge of the screw connecting chamber 11 is connected with the outer edge of each of the rotating screws 10. The rotating screws 10 are all provided with rotating wheels. A rotating wheel on one of the rotating screws 10 is a main rotating wheel 13. The driving motor 9 is in transmission connection with the main rotating wheel 13. A driving belt 12 is connecting all the rotating screws 10.

In some examples, the number of rotating screw 10 is at least four. For illustration only, there are four rotating screws in FIG. 2. A plurality of rotating screws 10 can be evenly distributed along the same circumference of the PET detector fixing plate 2. The driving motor 9 and the main rotating wheel 13 are connected by a driving belt 14 of the main rotating wheel 13.

Figure 3:
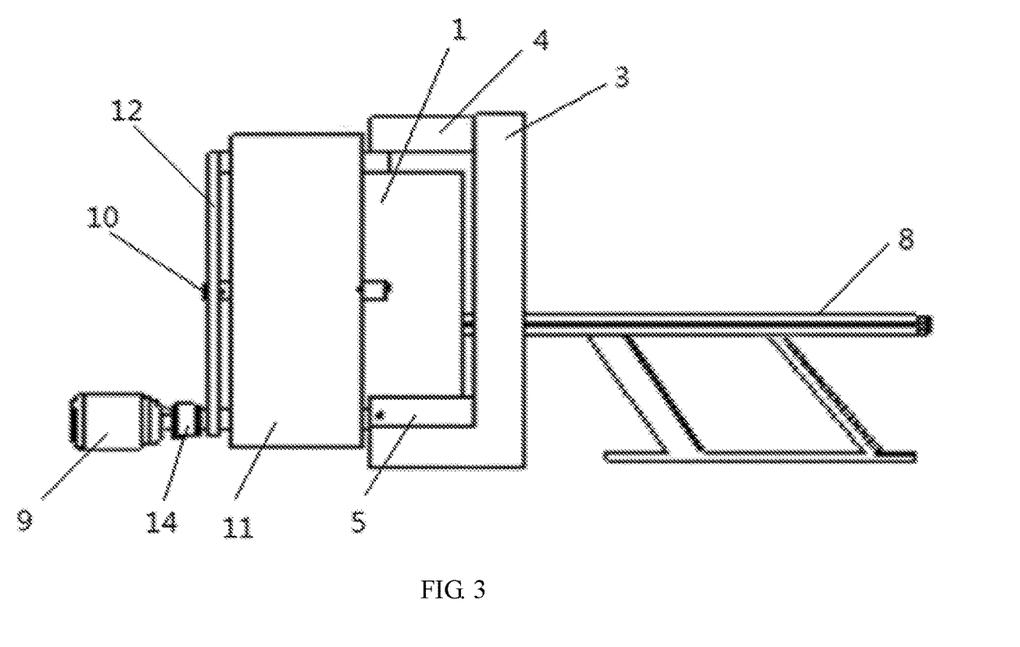
FIG. 3 is a structure schematic diagram of a forward state of a PET detector of the mechanical linkage system of PET and CT shown in FIG. 1.

After the CT host 21 finishes CT scanning, the transmission device 22 advances the PET detector 1 forward. The rotation of the driving motor 9 drives the driving belt 14 of the main rotating wheel 13 to rotate, the driving belt 14 of the main rotating wheel 13 drives the main rotating wheel 13 of the one of the rotating screws 10 at the bottom to rotate, the rotation of the main rotation wheel 13 drives the transmission of the driving belt 12, and the transmission of the driving belt 12 drives the rotating wheels of other rotating screws 10 to rotate so as to realize the simultaneous rotation of all of the rotating screws 10, thereby driving the PET detector fixing plate 2 to move to realize the forward and backward movement of the PET detector 1. As shown in FIG. 3, the PET detector 1 is ultimately in the scanning field of view of the CT host. After the PET detector 1 finishes PET scanning, the PET detector is moved by the transmission device 22 to return to its original position.

In some embodiments, the driving motor 9 and the main rotating wheel 13 are connected by a gear, and the rotation of the driving motor 9 drives the rotation of the main rotating wheel 13 by the gear.

Figure 4:
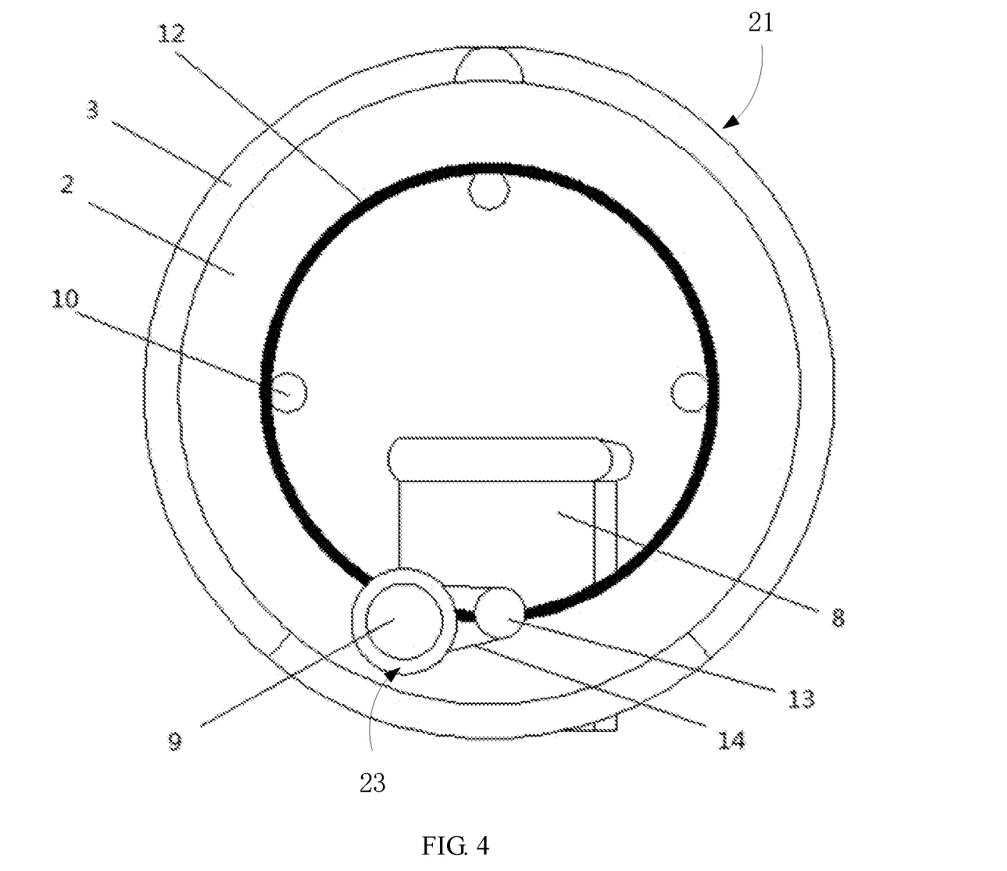
FIG. 4 is a structure schematic diagram of a left side structure of a mechanical linkage system of PET and CT in accordance with another example of the present disclosure.

FIG. 4 shows another example of the mechanical linkage system. In the illustrated embodiment, the transmission device 23 includes a driving motor 9, two or more rotating screws 10, and a driving belt 12. Compared to the system in FIG. 2, where each of the rotating screws 10 is connected to the outer side of the PET detector fixing plate 2 and the inner edge of the screw connecting chamber 11 is connected with the outer edge of each of the rotating screws 10, each of the rotating screws 10 in FIG. 4 is connected to the inner side of the PET detector fixing plate 2. In this way, the rotating screws 10 are installed on the inner side of the PET detector 1 without need for adding the screw connecting chamber 11, so that a scanning aperture of PET may be increased.

The rotating screws 10 are all provided with rotating wheels. A rotating wheel on one of the rotating screws 10 is the main rotating wheel 13. The driving motor 9 is in transmission connection with the main rotating wheel 13. A driving belt 12 is connecting all the rotating screws 10.

After the CT host 21 finishes CT scanning, the transmission device 23 advances the PET detector 1 forward. The rotation of the driving motor 9 drives the driving belt 14 of the main rotating wheel 13 to rotate, the driving belt 14 of the main rotating wheel drives the main rotating wheel 13 of the one of the rotating screws 10 at the bottom to rotate, the rotation of the main rotation wheel 13 drives the transmission of the driving belt 12, and the transmission of the driving belt 12 drives the rotating wheels of other rotating screws 10 to rotate so as to realize the simultaneous rotation of all of the rotating screws 10, thereby driving the PET detector fixing plate 2 to move to realize the forward and backward movement of the PET detector 1 so that the PET detector 1 is ultimately in the scanning field of view of the CT host 21. After the PET detector 1 finishes PET scanning, driven by the transmission device 23, the PET detector 1 returns to its original position.

Figure 8:
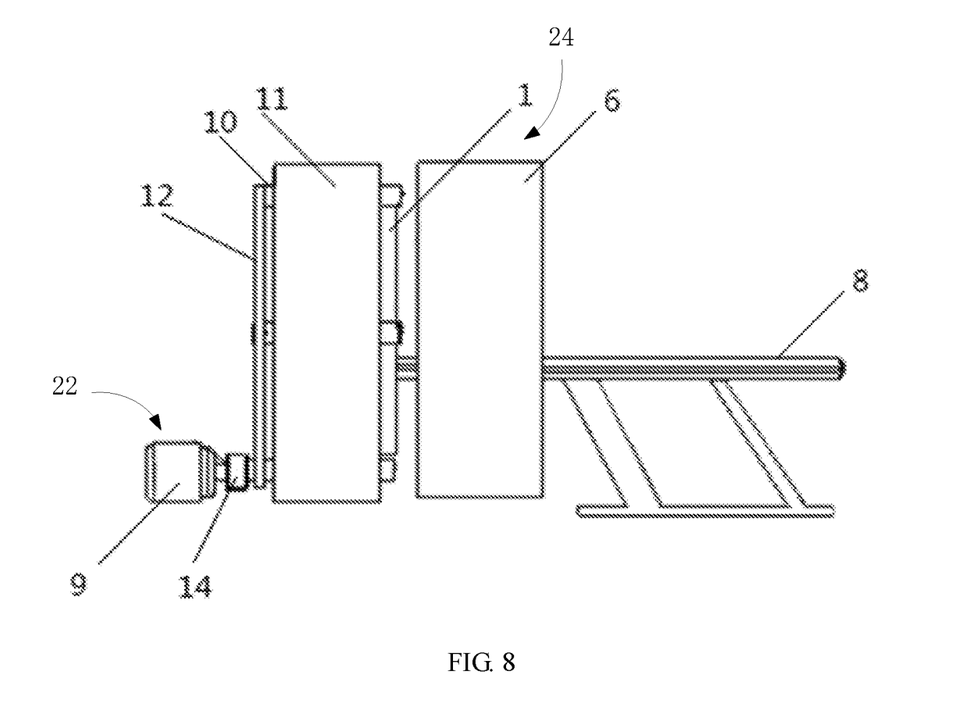
FIG. 8 is a structure schematic diagram of a mechanical linkage system of PET and MRI in accordance with one example of the present disclosure.

The CT hosts 21 in the above embodiments may be replaced with an MRI host. As shown in FIG. 8, an MRI host 24 includes an MRI magnet 6 with an aperture larger than that of the PET detector 1.

Figure 9:
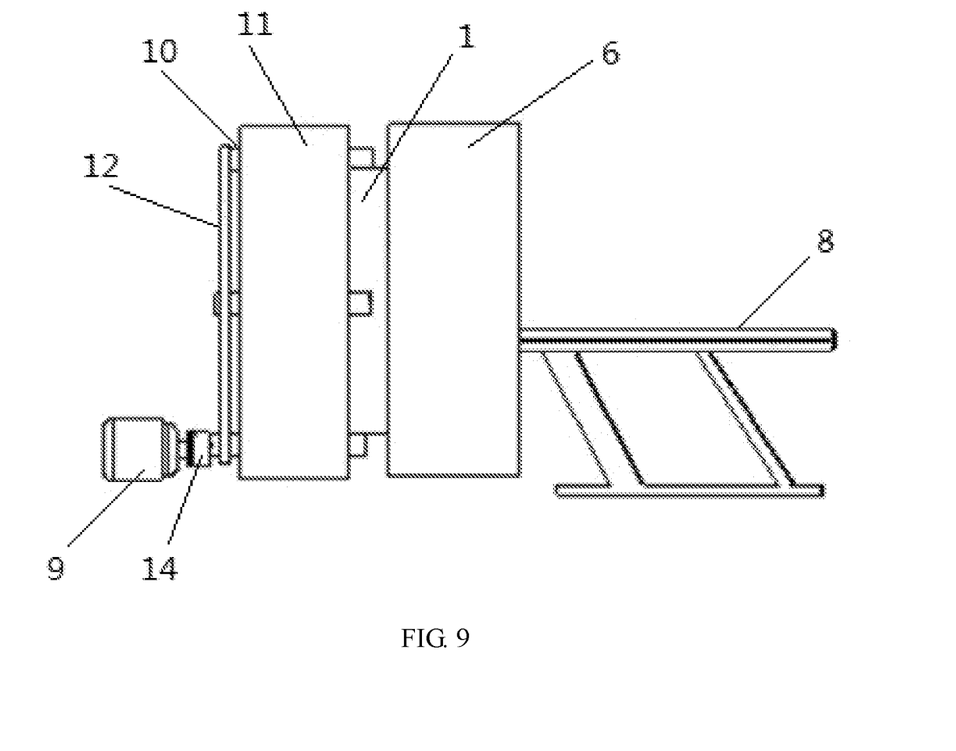
FIG. 9 is a structure schematic diagram of a forward state of a PET detector shown in FIG. 8.

After the MRI host 24 finishes MRI scanning, the transmission device 22 advances the PET detector 1 forward. The rotation of the driving motor 9 drives the driving belt 14 of the main rotating wheel to rotate, the driving belt 14 of the main rotating wheel drives the main rotating wheel 13 of the rotating screw 10 at the bottom to rotate, the rotation of the main rotation wheel 13 drives the transmission of the driving belt 12, and the transmission of the driving belt 12 drives the rotating wheels of other rotating screws 10 to rotate to realize the simultaneous rotation of all of the rotating screws 10, thereby driving the PET detector fixing plate 2 to move to realize the forward and backward movement of the PET detector 1. As shown in FIG. 9, the PET detector 1 is ultimately in a scanning field of view of the MRI magnet 6. After the PET detector 1 finishes PET scanning, driven by the transmission device 22, the PET detector 1 returns to its original position.

Figure 5:
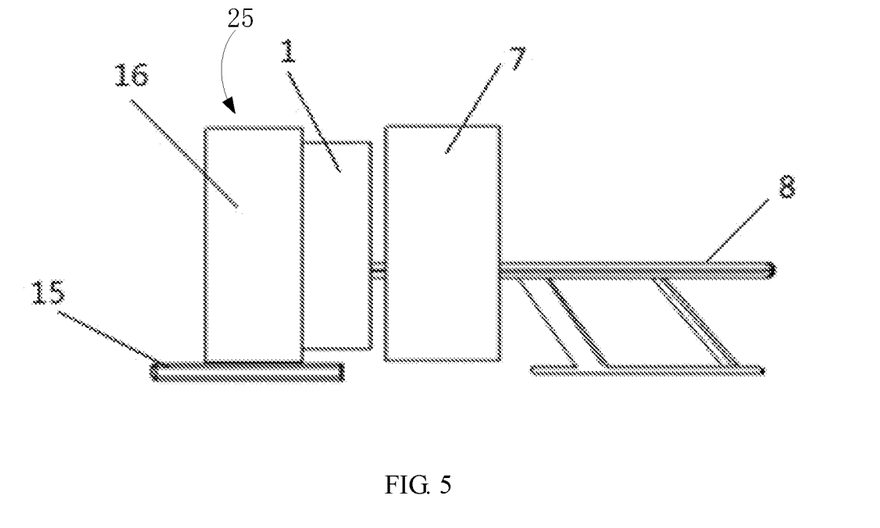
FIG. 5 is a structure schematic diagram in which a movable base is installed at a bottom of a PET host in accordance with one example of the present disclosure.

As shown in FIG. 5, in the illustrated embodiment, the PET host 25 further includes a PET detector connecting chamber 16, and the PET detector 1 is connected inside the PET detector connecting chamber 16. A moving system includes a movable base 15 installed at the bottom of the PET host.

After a CT/MRI host 7 (which may be the CT host 21 or the MRI host 24) finishes CT or MRI scanning, a PET host 25 is moved forward or backward by moving the movable base 15, and the PET detector 1 is ultimately in the scanning field of view of the CT host or MRI host, so as to realize scanning with a common field of view. After the PET detector 1 finishes PET scanning, the PET detector 1 is returned to its original position by moving the movable base 15.

Figure 6:
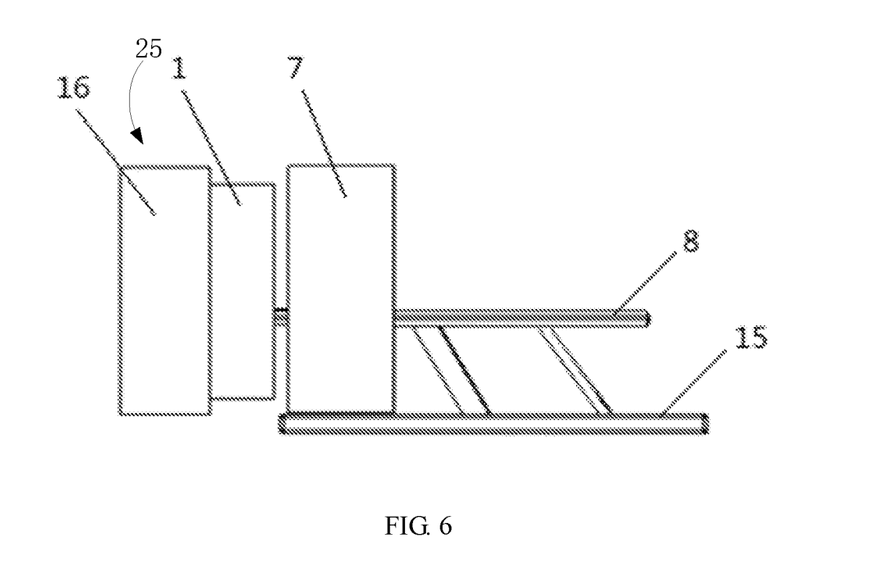
FIG. 6 is a structure schematic diagram in which a movable base is installed at bottoms of a CT host and a scanning bed in accordance with one example of the present disclosure.

As shown in FIG. 6, in the illustrated embodiment, the PET host 25 further includes a PET detector connecting chamber 16 and the PET detector 1 is connected inside the PET detector connecting chamber 16. The moving system includes the movable base 15 installed at the bottoms of both the CT/MRI host 7 and the scanning bed 8.

After the CT/MRI host 7 finishes CT or MRI scanning, the CT/MRI host 7 and the scanning bed 8 are moved forward or backward by moving the movable base 15, and the PET detector 1 is ultimately in the scanning field of view of the CT host or MRI host so as to realize scanning with a common field of view. After the PET detector 1 finishes PET scanning, the CT/MRI host 7 and the scanning bed 8 are returned to their original positions by moving the movable base 15.

Figure 7:
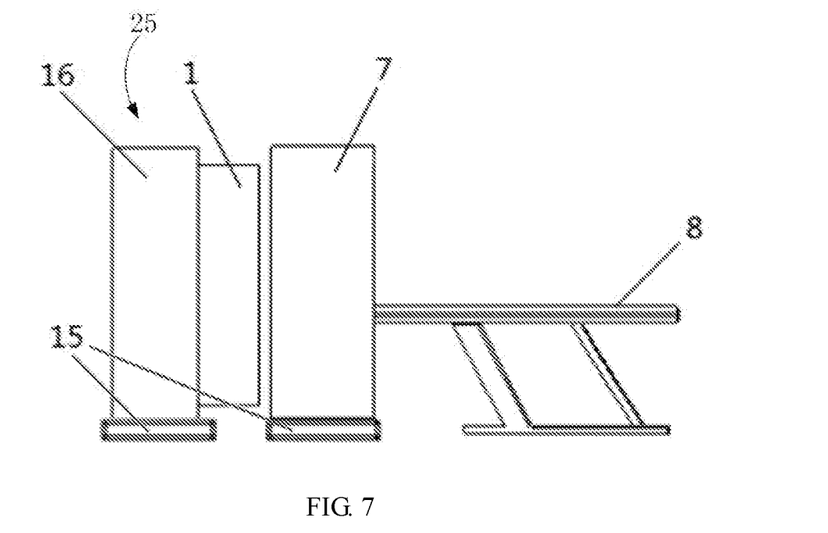
FIG. 7 is a structure schematic diagram in which two movable bases are installed at bottoms of a PET host and a CT host, respectively, in accordance with one example of the present disclosure.

As shown in FIG. 7, in the illustrated embodiment, the PET host 25 further includes the PET detector connecting chamber 16, and the PET detector 1 is connected inside the PET detector connecting chamber 16. The moving system includes two movable bases 15 installed at the bottoms of the PET host and the CT/MRI host 7, respectively.

After the CT/MRI host 7 finishes CT or MRI scanning, the PET host 25 and the CT/MRI host 7 are moved toward each other at the same time by moving the two respective movable bases 15 towards each other, and the PET detector 1 is ultimately in the scanning field of view of the CT host or MRI host so as to realize scanning with a common field of view. After the PET detector 1 finishes PET scanning, the PET host 25 and the CT/MRI host 7 are moved in opposite directions by moving the two movable bases 15 so as to return to their original positions. As a non-limiting example, the movable bases may be provided on a guiding rail and the moving of one or more of the movable bases may be achieved by a transmission of chains, belts or screws.

Implementations of the present disclosure further provide a linkage scanning method. The method can include: performing a pilot image scanning of CT/MRI; performing a CT helical scanning or an MRI axial scanning; moving a PET detector of a PET host to be in the scanning field of view of a CT/MRI host by the displacement of a moving system after CT/MRI scanning is completed; starting collecting PET data; and moving the PET detector to be out of the scanning field of view of the CT/MRI host by the moving system after the PET data collection is completed.

Figure 10:
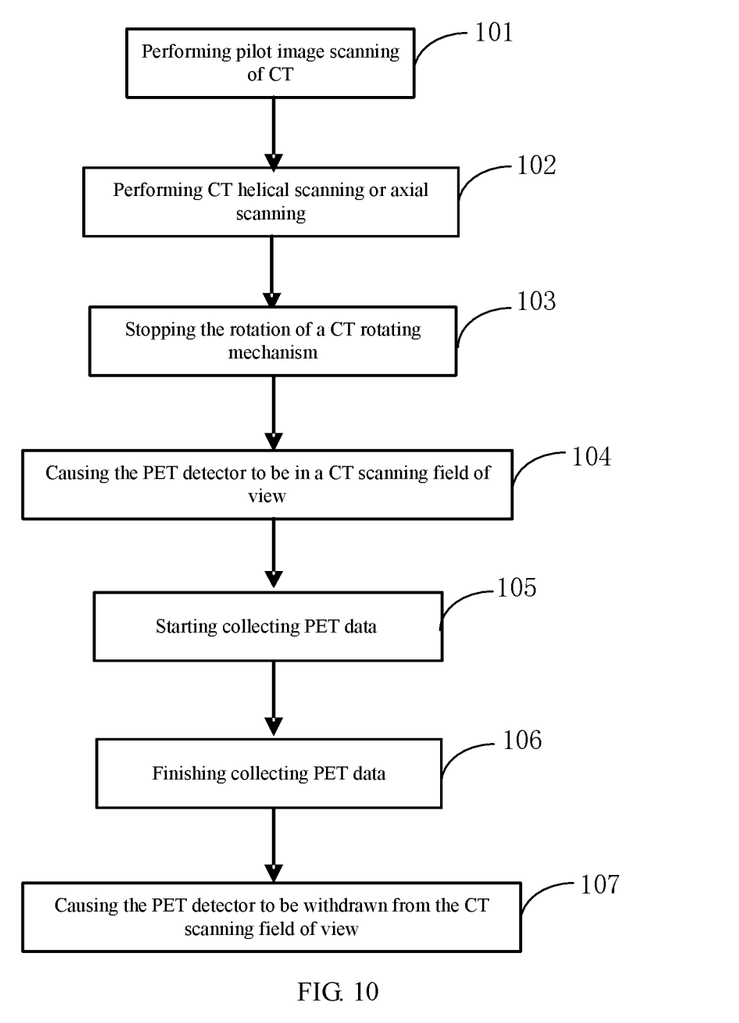
FIG. 10 is a flow chart of a PET-CT linkage scanning method in accordance with one example of the present disclosure.

As shown in FIG. 10, when the CT/MRI host includes a CT host, a scanning process is as follows: first performing a pilot image scanning of CT (101); then performing a CT helical scanning or an axial scanning (102); stopping the rotation of a CT rotating system after finishing the CT helical scanning or the axial scanning (103); moving the PET detector of a PET host to be in a CT scanning field of view by the displacement of the moving system (104); starting collecting PET data (105); finishing collecting PET data (106); and moving the PET detector to be out of the CT scanning field of view by the moving system (107).

Figure 11:
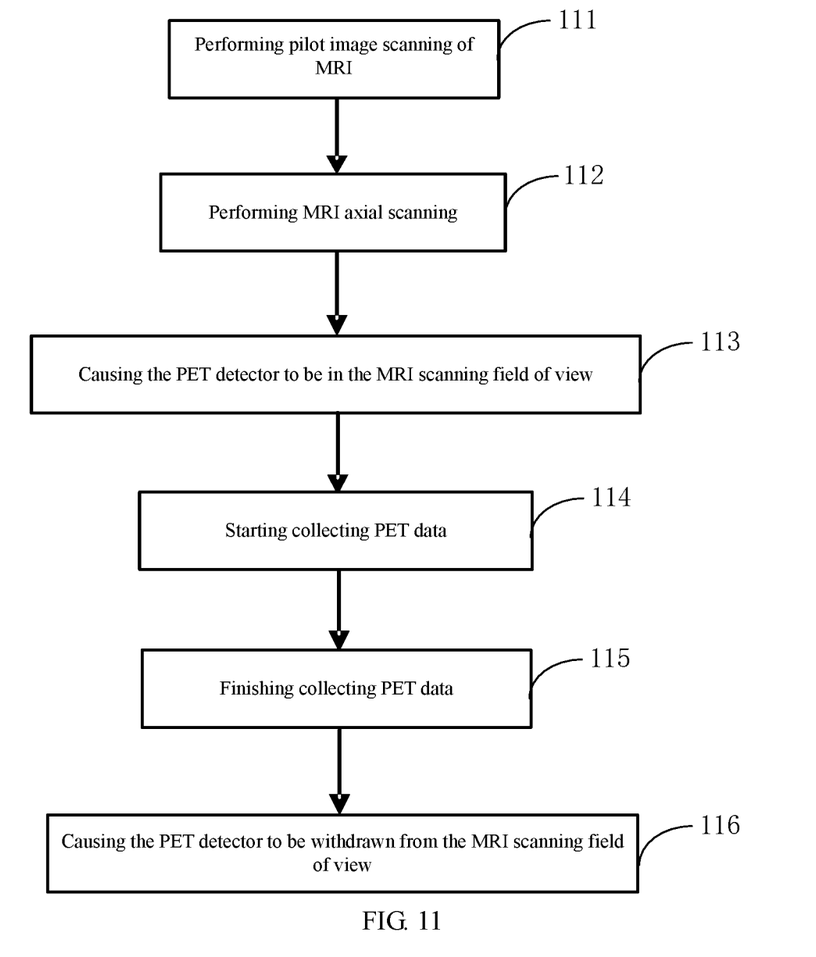
FIG. 11 is a flow chart of a PET-MRI linkage scanning method in accordance with one example of the present disclosure.

As shown in FIG. 11, when the CT/MRI host includes an MRI host, a scanning process is as follows: first performing a pilot image scanning of MRI (111); then performing an MRI axial scanning (112); moving the PET detector to be in the MRI scanning field of view by the displacement of the moving system after finishing MRI scanning (113); starting collecting PET data (114); finishing collecting PET data (115); and moving the PET detector to be out of the MRI scanning field of view by the moving system (116).

During the above scanning process, the PET detector is moved to be in the scanning field of view of the CT/MRI host by the displacement of the moving system.

In some examples, the moving system includes a transmission device connected with a PET detector fixing plate, the rotation of a driving motor drives a main rotating wheel to rotate by mechanical transmission, the rotation of the main rotating wheel drives a driving belt to rotate, and the driving belt drives rotating wheels of other rotating screws to rotate, so as to drive the PET detector fixing plate to move, so that the PET detector is moved back and forth. The driving motor and the main rotating wheel may be connected by the driving belt of the main rotating wheel, the rotation of the driving motor drives the driving belt of the main rotating wheel to rotate, the driving belt of the main rotating wheel drives the main rotating wheel to rotate. The driving motor and the main rotating wheel may also be connected by a gear, and the rotation of the driving motor drives the main rotating wheel to rotate through the gear.

In other examples, the moving system includes a movable base installed at the bottom of the PET host. The PET host is moved forward or backward by moving the movable base so that the PET detector is ultimately in the scanning field of view of the CT host or the MRI host.

In other examples, the moving system includes a movable base installed at the bottoms of both the CT/MRI host and the scanning bed. The CT/MRI host and the scanning bed are moved forward by moving the movable base so that ultimately the PET detector is in the scanning field of view of the CT host or the MRI host.

In other examples, the moving system includes two movable bases installed at the bottoms of the PET host and the CT/MRI host, respectively. The PET host and the CT/MRI host are moved towards each other by moving the two movable bases so that ultimately the PET detector is in the scanning field of view of the CT/MRI host.

For simplicity and illustrative purposes, the present disclosure is described by referring mainly to examples thereof. In the above description, numerous specific details are set forth to provide a thorough understanding of the present disclosure. It will be readily apparent however, that the present disclosure may be practiced without limitation to these specific details. In other instances, some methods and structures have not been described in detail so as not to unnecessarily obscure the present disclosure.

The present disclosure has been described in detail with reference to the specific embodiments shown in the accompanying drawings. However, these embodiments are not intended to limit the present disclosure. Any changes in structures, methods, or functions made by those skilled in the art in accordance with these embodiments are included within the scope of protection of the present disclosure.

It is to be understood that although different structures may be described using the terms such as a first, a second, etc. in the present disclosure, these structures should not be limited to these terms. These terms are used only to distinguish the same type of structures from each other. For example, a first host may also be referred to as a second host without departing from the scope of the present disclosure, and similarly, a second host may also be referred to as a first host depending on the context.

The terminology used in the present disclosure is for the purpose of describing particular embodiments only, and is not intended to be limiting of the present disclosure. The singular forms such as "a", 'said", and "the" used in the present disclosure and the appended claims are also intended to include a plural form, unless the context clearly indicates otherwise. It is also to be understood that the term "and/or" as used herein refers to any or all possible combinations that include one or more associated listed items. The term "based on" means based at least in part on. The term "include", or variations such as "includes" or "including", will be understood to imply the inclusion of a stated element, integer or block, or group of elements, integers or blocks, but not the exclusion of any other element, integer or block, or group of elements, integers or blocks.

Other embodiments of the present disclosure will readily occur to those skilled in the art upon consideration of the specification and practice of the present disclosure disclosed herein. The present disclosure is intended to cover any variations, uses or adaptations of the present disclosure, which are subject to the general principles of the present disclosure and include the general knowledge or conventional technical means in the technical field that the present disclosure has not disclosed. The specification and embodiments are to be regarded as illustrative only, and the true scope and spirit of the present disclosure are indicated by the claims of the present disclosure.

It is to be understood that the present disclosure is not limited to the precise structure described above and shown in the accompanying drawings, and that different modifications and alterations may be made without departing from the scope thereof. The scope of the present disclosure is limited only by the appended claims.

The invention claimed is:

1. A mechanical linkage system of Positron Emission Tomography (PET) and Computed Tomography/Magnetic Resonance Imaging (CT/MRI), the system comprising:
a PET host having a PET detector and a PET detector fixing plate on which the PET detector is installed;
a CT/MRI host including one of a CT host and an MRI host disposed opposite to the PET host, wherein the CT/MRI host has an aperture larger than an aperture of the PET detector;
a scanning bed located at an end of the CT/MRI host; and
a moving system connected with the PET detector fixing plate and configured such that the PET detector is operable to be moved into or out of a scanning field of view of the CT/MRI host along a direction perpendicular to the PET detector fixing plate,
wherein the moving system comprises:
a driving motor,
a screw connecting chamber,
two or more rotating screws distributed around an outer circumference of the PET detector fixing plate and around an inner circumference of the screw connecting chamber, each of the rotating screws being in direct connection with the outer circumference of the PET detector fixing plate without going through the PET detector fixing plate and in direct connection with the inner circumference of the screw connecting chamber, each of the rotating screws being rotatable about a respective axis parallel to the direction perpendicular to the PET detector fixing plate,
respective rotating wheels installed on the rotating screws, wherein a rotating wheel on one of the rotating screws is a main rotating wheel, and the driving motor is in transmission connection with the main rotating wheel, and
a driving belt connecting the rotating screws.

2. The system of claim 1, wherein the CT host comprises:
a CT rotation system having an aperture larger than the aperture of the PET detector;
a CT tube installed on an end of the CT rotation system and adjacent to the PET detector; and
a CT detector installed on the end of the CT rotation system and adjacent to the PET detector, the CT detector being disposed opposite to the CT tube.

3. The system of claim 1, wherein the MM host comprises an MRI magnet having an aperture larger than the aperture of the PET detector.

4. The system of claim 1, wherein
an outer edge of each of the rotating screws is connected with a respective inner edge of the screw connecting chamber.

5. The system of claim 1, wherein the driving motor and the main rotating wheel are connected by one of a second driving belt of the main rotating wheel and a gear.

6. The system of claim 1, wherein the rotating screws are evenly distributed along the outer circumference of the PET detector fixing plate.

7. The system of claim 1, wherein the PET detector fixing plate is in a form of a ring structure.

8. A linkage scanning method comprising:
performing a pilot image scanning with a CT/MRI host;
performing a CT helical scanning or an MRI axial scanning with the CT/MRI host;
moving a PET detector of a PET host along a first direction to be in a scanning field of view of the CT/MRI host by a displacement of a moving system;
collecting PET data with the PET detector; and
after the PET data collection is completed, moving the PET detector along a second, opposite direction to be out of the scanning field of view of the CT/MRI host by the moving system, wherein the PET host comprises a PET detector fixing plate on which the PET detector is installed, the first direction being perpendicular to the PET detector fixing plate, and wherein the moving system comprises:
- a driving motor,
- a screw connecting chamber,
- two or more rotating screws of distributed around an outer circumference of the PET detector fixing plate and around an inner circumference of the screw connecting chamber, each of the rotating screws being in direct connection with the outer circumference of the PET detector fixing plate without going through the PET detector fixing plate and in direct connection with the inner circumference of the screw connecting chamber, each of the rotating screws being rotatable about a respective axis parallel to the first direction perpendicular to the PET detector fixing plate,
- respective rotating wheels installed on the rotating screws, wherein a rotating wheel on one of the rotating screws is a main rotating wheel, and the driving motor is in transmission connection with the main rotating wheel, and
- a first driving belt connecting the rotating screws.

9. The linkage scanning method of claim 8,
wherein moving the PET detector to be in the scanning field of view of the CT/MRI host by the displacement of the moving system comprises:
driving a second driving belt of the main rotating wheel to rotate by a rotation of the driving motor,
driving the main rotating wheel and thus the rotating screw on which the main rotating wheel is installed to rotate by the second driving belt of the main rotating wheel,
driving the first driving belt by the rotation of the main rotating wheel, and
driving rotating wheels installed on the other rotating screws and thus the other rotating screws to rotate by the first driving belt, so as to drive the PET detector fixing plate to move, such that the PET detector is moved forward or backward to ultimately be in the scanning field of view of the CT/MRI host.

10. The linkage scanning method of claim 8,
wherein moving the PET detector to be in the scanning field of view of the CT/MRI host by the displacement of the moving system comprises:
driving the main rotating wheel and thus the rotating screw on which the main rotating wheel is installed to rotate by a rotation of a driving motor through a gear,
driving the first driving belt by the rotation of the main rotating wheel, and
driving rotating wheels of the other rotating screws and thus the other rotating screws to rotate by the first driving belt, so as to drive the PET detector fixing plate to move, such that the PET detector is moved forward or backward to ultimately be in the scanning field of view of the CT/MRI host.

11. The linkage scanning method of claim 8, wherein the PET detector fixing plate is in a form of a ring structure.

12. The linkage scanning method of claim 8, wherein the rotating screws are evenly distributed along the outer circumference of the PET detector fixing plate.

13. A mechanical linkage system of Positron Emission Tomography (PET) and Computed Tomography/Magnetic Resonance Imaging (CT/MRI), the system comprising:
- a PET host having a PET detector and a PET detector fixing plate on which the PET detector is installed;
- a CT/MRI host including one of a CT host and an MRI host disposed opposite to the PET host, wherein the CT/MRI host has an aperture larger than an aperture of the PET detector;
- a scanning bed located at an end of the CT/MRI host; and
- a moving system connected with the PET detector fixing plate and configured such that the PET detector is operable to be moved into or out of a scanning field of view of the CT/MRI host along a direction perpendicular to the PET detector fixing plate, wherein the moving system comprises:
- a driving motor,
- two or more rotating screws distributed around an inner circumference of the PET detector fixing plate, each of the rotating screws being connected with the inner circumference of the PET detector fixing plate without going through the PET detector fixing plate, each of the rotating screws being rotatable about a respective axis parallel to the direction perpendicular to the PET detector fixing plate,
- respective rotating wheels installed on the rotating screws, wherein a rotating wheel on one of the rotating screws is a main rotating wheel, and the driving motor is in transmission connection with the main rotating wheel, and
- a driving belt connecting the rotating screws.

14. The system of claim 13, wherein the CT host comprises:
- a CT rotation system having an aperture larger than the aperture of the PET detector;
- a CT tube installed on an end of the CT rotation system and adjacent to the PET detector; and
- a CT detector installed on the end of the CT rotation system and adjacent to the PET detector, the CT detector being disposed opposite to the CT tube.

15. The system of claim 13, wherein the MRI host comprises an MM magnet having an aperture larger than the aperture of the PET detector.

16. The system of claim 13, wherein the driving motor and the main rotating wheel are connected by one of a second driving belt of the main rotating wheel and a gear.

17. The system of claim 13, wherein the rotating screws are evenly distributed along the inner circumference of the PET detector fixing plate.

18. The system of claim 13, wherein the PET detector fixing plate is in a form of a ring structure.

* * * * *